(12) United States Patent
Note-Simonnard

(10) Patent No.: US 6,461,638 B1
(45) Date of Patent: Oct. 8, 2002

(54) LAXATIVE COMPOSITIONS AND METHOD FOR MAKING SAME

(75) Inventor: Axelle Note-Simonnard, Monaco (MC)

(73) Assignee: Techni-Pharma (MC)

( * ) Notice: Subject to any disclaimer, the term of this patent is extended or adjusted under 35 U.S.C. 154(b) by 0 days.

(21) Appl. No.: 08/973,452

(22) PCT Filed: Mar. 28, 1997

(86) PCT No.: PCT/FR97/00567
§ 371 (c)(1),
(2), (4) Date: May 25, 1999

(87) PCT Pub. No.: WO97/36575
PCT Pub. Date: Oct. 9, 1997

(30) Foreign Application Priority Data

Apr. 1, 1996 (FR) ............................... 96 04041

(51) Int. Cl.$^7$ ..................... A61K 9/46; A61K 33/00; A61L 9/04
(52) U.S. Cl. ................... 424/466; 424/44; 424/717; 514/766

(58) Field of Search ................ 424/44, 717, 278.1, 424/466; 514/620, 966

(56) References Cited

U.S. PATENT DOCUMENTS

| | | | | |
|---|---|---|---|---|
| 3,764,668 A | * | 10/1973 | Higuchi et al. | ................ 424/44 |
| 4,451,454 A | * | 5/1984 | Wong | ......................... 424/717 |
| 4,855,283 A | * | 8/1989 | Lockhoff et al. | ........ 424/278.1 |
| 5,468,504 A | * | 11/1995 | Schaeffer | .................... 424/466 |
| 5,629,347 A | * | 5/1997 | Swain et al. | ................. 514/620 |

* cited by examiner

Primary Examiner—Thurman K. Page
Assistant Examiner—Blessing Fubara
(74) Attorney, Agent, or Firm—Bierman, Muserlian and Lucas

(57) ABSTRACT

Pharmaceutical compositions for rectal administration comprising an effervescent mixture comprising sodium bicarbonate and glutamic acid or pyroglutamic acid with at least one diluent adapted for rectal administration, said mixture being effervescent.

8 Claims, 1 Drawing Sheet

LAXATIVE COMPOSITIONS AND METHOD FOR MAKING SAME

Figure 1:
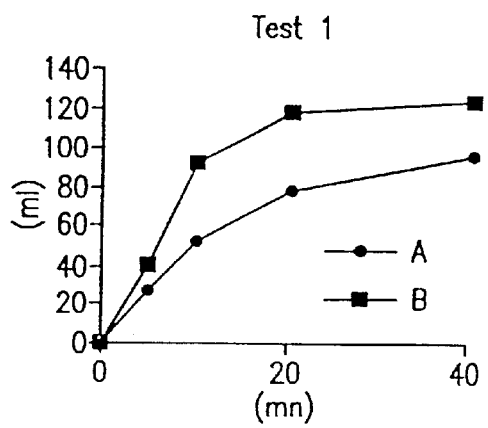
Figure 2:
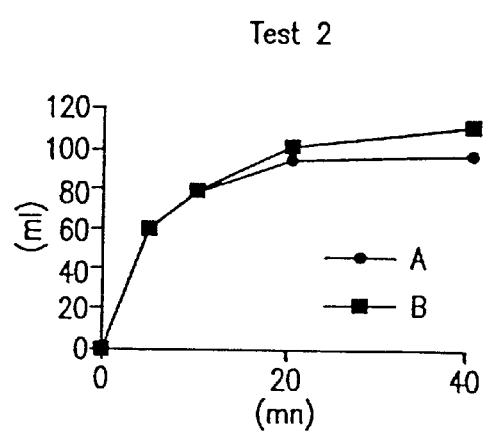
Figure 3:
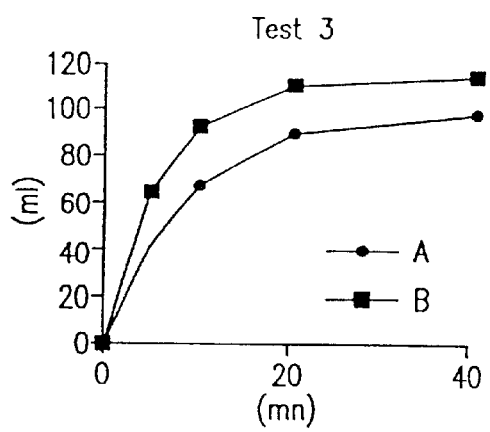
Figure 4:
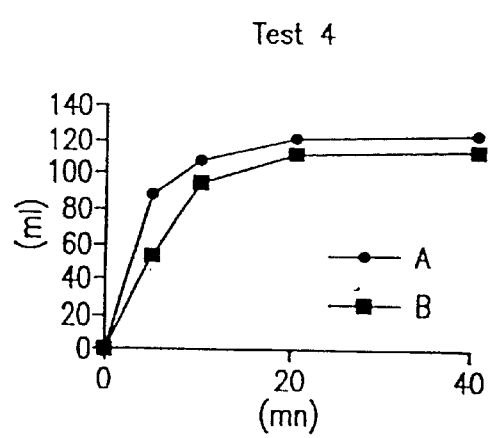
Figure 5:
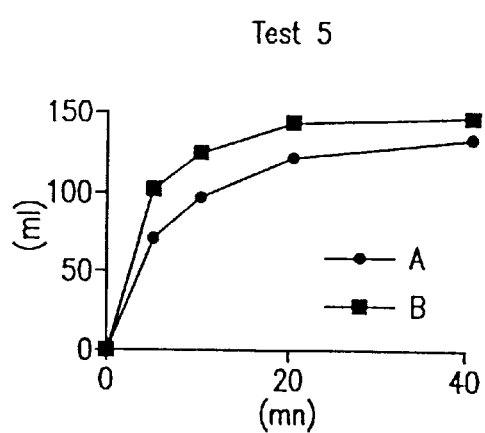

The present invention reports to the therapeutic chemistry domain and more particularly to pharmacotechny.

It is more precisely related to new pharmaceutical compositions with laxative properties whom the main characteristic is to contain an effervescent mixture producing fast and gradually carbon dioxide.

The invention specifically reports to new pharmaceutical compositions designed for the rectal route able to producing by a chemical reaction active principles in contact with humidity existing in the rectal ampule an important and quick gaseous release.

The French patent number 788.198 (Waldenmeyer J. G.) has already described a process to obtain effervescent suppositories which offer the possibility to release native carbon dioxide under action of humidity, heat or any other reason in which the raw materials releasing this acid by their mixing are coated for protection in a greasy substance which thus avoid a premature chemical reaction and consequently protect against decomposition.

Meanwhile these suppositories contain in their bulk, hydrophilic ingredients which allow to the biologic fluids to penetrate into the bulk and allow the start of the chemical reaction which involves the physiologic effect.

Later on the French patent application number 94.11913 filled on Oct. 5, 1994 by the Applicant has described a new process to manufacture such effervescent suppositories on a potassium tartrate acid and sodium bicarbonate basis, stable during preservation.

The problem which occurred for the realization of suppositories described in the previous literature has been to be able to form a sufficiently effervescent bulk, i.e. to release a sufficiently important volume of carbonic gas in a sufficiently reduced set of time to obtain a marked distension of coasts of the rectal ampoule, which produce a relieving reflex.

Different solutions exist to try to solve this problem. The first solution consists to enhance the amount of reactive active principles to increase the released volume of carbonic gas. Meanwhile the size of a suppository rapidly reaches a limit and so it is not possible to incorporate more active ingredients without changing the conservation and homogeneity of the suppositories.

The other solution consists to incorporate into the mass of the pharmaceutical composition intended to the rectal route, another acid component more reactive than potassium acid tartrate and offering all the required guarantees about local tolerance and lack of toxicological risk whom the limit remains in the necessity to do not generate a too coarse release of carbon dioxide.

This solution lies as a basis for the invention which is the subject of the present application.

Therefore the invention consists in pharmaceutical compositions intended to the rectal route, formed with an effervescent mixture consisting of an alkali-metal bicarbonate and a determined acid reactive compound, selected in the group formed by monosodium or monopotassium phosphate, monosodium citrate, pyroglutamic acid and glutamic acid, associated or admixed with one or more diluents or vehicles adapted to the realization of a pharmaceutical form intended to the rectal route.

The effervescent formulation calls for the presence of an alkaline element liable to release easily carbonic gas by a chemical reaction with an acid compound. The experiment shows that with alkaline or alkaline earth metal or others metals carbonates, the reaction is much slower and rarely complete in a relatively short set of time. By another way the selection of the acid compound needs to take considerations of two conditions. This acid compound must not be irritant or toxic on the one hand, and does not launch a too violent or fast effervescent reaction in contact with the alkaline agent. There are only a limited number of acid compounds which satisfy to these both conditions. Among the factors which can involve for the respect of these conditions, there is firstly the pka of the used acid compound and on the other hand the solubility of the acid compound in water or in the biological environment. Thus, a compound like benzoic phtalimide or succinimide due to their low solubility in water only induces a reduced and delayed release. It is also possible that their low degree of acidity play some part.

At the contrary the incorporation in the mixture of strong acid compounds or very soluble acids in aqueous mediums lead to a very strong or too fast gaseous release which exclude the use of such compounds.

Thus, it is not possible to use any acid compound if it does not fall into the category defined above and this fact requires a preliminary adjustment to determine whether the acidic compound is suitable for such a use.

About pharmaceutical compositions intended to the rectal use suppositories made with a synthetic or natural greasy matrix are indicated firstly, and also rectal capsules realized with gelatine. Others solid or coated forms of administration by rectal route, can also be considered.

According to the needs, the acid compound content will be that which also approximately agrees on the molar level with the formulation defined in the previous application in France number 94.11913 by the applicant, namely 1.150 g potassium acid tartrate with 0.700 g of bicarbonate sodium for an adult suppository, i.e. preferably between 1.15 g and 1.20 g, 1.184 g for monosodium phosphate, between 1.25 and 1.30 g and preferably 1.2847 g for monosodium citrate, or for a diacid substance as glutamic acid, between 0.85 and 0.90 g and preferably 0.878 g and for pyroglutamic acid between 0.85 and 0.90 g and preferably 0.889 g. Under these conditions the mixture is able to release a measured volume of $CO_2$ determined with the Bernard's calcimeter, under atmospheric pressure, about 100 to 120 ml for a suppository during 20 minutes.

The study of the carbonic gas release shows that during the first five minutes a maximal gaseous release occurred which represents about 80% of the total release. Then the release slows down to reach an asymptomatic value after 10 minutes, and after 20 minutes the variations of volume become very small. Depending on the nature of the acid agent, this gaseous release can be very fast and nearly complete after 5 minutes or on the contrary remaining small and needing more than 40 minutes to reach its achievement. Therefore, it is between these two utmost values that the therapeutic optimum takes place.

This invention is also related to a process of realization of pharmaceutical compositions intended for the rectal route, which consist to blend an acid reactive salt selected among monosodium phosphate, monopotassium phosphate, monosodium citrate, pyroglutamic acid and glutamic acid and an alkali-metal bicarbonate with an hydrophilic excipient then to an opacifiant agent and this mixture is introduced in a fusible greasy excipient near the body temperature.

In a particular mode of realization, the hydrophilic excipient is preferably an animal or vegetable lecithin, as for example Soya lecithin or yolk lecithins.

The opacifiant agent is a mineral product, in a powder form, insoluble in the hydrophilic excipient and in the greasy excipient. The opacifiant agent will be preferably an aluminium silicate, a magnesium silicate, a titan oxide or silica. The greasy excipient is a grease with a melting point lying around 40° C., like cocoa-butter, shea butter, *Bassia longifolia* (*Oleum bassiae*) butter or mixtures of them or a polyacohol stearate like a semi-synthetic or synthetic polyethyleneglycol or glyceryl stearate, the melting point of which is situated in this temperature range like polyethyleneglycol stearate commercialised under the denomination Trade Name LABRAFIL and semi-synthetic glycerids described in the French Pharmacopea 10$^{th}$ edition and commercialised under the appellation Trade Name SUPPOCIRE® . . .

Considering rectal capsules, greasy excipient is not used or only in small amounts to secure an homogeneous solid bulk. This preparation is introduced into a gelatine capsule the thickness of which varies from 1 to 3 mm.

The following examples illustrate the main characteristics of the invention without limiting them.

Effervescence Measure by Release of $CO_2$

Working of the Bernard's calcimeter.

The assay consists in verifying the working of the equipment of the Bernard's calcimeter.

Material a 500 ml flask a graduated tube until 200 ml a glass tube a 250 ml flat-bottomed flask, with an inclined lateral neck, at 30° C.

a rubber stopper perforated by a hole for the neck of the flask a full rubber stopper for the lateral neck supporting a capsule for powders and suppositories a magnetic heating stirrer a saturated sodium chloride solution Modification A little modification has been made on the rubber stopper of the lateral neck by adding a tap. This addition is necessary until at time 0, the experiment begins with an inner pressure equal to the atmospheric pressure.

Installation

Hang the flask and the graduated tube to a support

Connect the flask and the bottom of the graduated tube with a pipe, allowing the connection of the saturated Na chloride solution between the two installations Connect the top of the graduated tube and the reaction flask with a glass tube across which the $CO_2$ rises from the flask Mode of Operation Introduce a saturated sodium chloride solution in the flask and the graduated tube Adjust the level of the graduated tube before starting the experiment Lay on the magnetic heating stirrer the flask containing 100 ml of distilled water at 37° C.

Fill up the flask with a stopper previously fixed at the end of the releasing tube of $CO_2$ Introduce the suppository in the flask without contact occurring between the suppository and the water Verify again the sodium chloride level in the graduated tube before turning off the tap of the side stopper Turn off the tap Turn on the stirrer and drop the suppository, without forget to unlock the chronometer The experiment takes place at the temperature of the laboratory (about 20° C.).

Intensity of the Reaction Between the Basic Compounds

This ASSAY is made on the two basic active principles with respect to the amounts of each product according to the industrial formula.

Mode of Operation

| ASSAY 1 | |
|---|---|
| Time (minutes) | ml |
| 1 | 2,5 |
| 2 | 49,2 |
| 3 | 66,8 |
| 4 | 73 |
| 5 | 83,2 |
| 6 | 94,6 |
| 7 | >100 |

Weigh exactly the required amounts for the two active principles for one suppository. Mix manually and make the experiment.

| Sodium bicarbonate | 0.700 g |
|---|---|
| Potassium acid tartrate | 1.150 g |

Manufacture of the Suppositories 10 batches have been produced according the industrial protocol and assayed the same day.

The suppositories remain insoluble at the temperature of the laboratory (20° C.) during the study of the release of $CO_2$. Thus, it is necessary to heat the water until 37° C. Thus a magnetic heating stirrer has been used.

The Reference Curve of Two Active Principles at 37° C. has been Made Again

Proportions for Suppositories for Adults:
Na bicarbonate 0.700 g
K acid tartrate 1.150 g

| | number of experiments 5 | | | | | |
|---|---|---|---|---|---|---|
| | ASSAY 1 | ASSAY 2 | ASSAY 3 | ASSAY 4 | ASSAY 5 | AVERAGE |
| Time | ml | ml | ml | ml | ml | ml |
| 1 | 44.2 | 43 | 42.6 | 44.2 | 44.8 | 43.76 |
| 2 | 57.8 | 56.2 | 50 | 62 | 61.3 | 57.46 |
| 3 | 67.2 | 65.8 | 63.4 | 72.6 | 70.8 | 67.96 |
| 4 | 73.3 | 73.2 | 72.2 | 79.1 | 77.2 | 75.1 |
| 5 | 78.8 | 78.6 | 78.5 | 84.2 | 81.8 | 80.38 |
| 6 | 82.7 | 82.6 | 83.4 | 87.8 | 85.4 | 84.38 |
| 7 | 85.8 | 85.9 | 87.3 | 90.6 | 88.2 | 87.56 |
| 8 | 88 | 88.5 | 90.2 | 92.9 | 90.2 | 89.96 |
| 9 | 91.2 | 90.8 | 92.3 | 94.6 | 92.2 | 92.22 |
| 10 | 92.2 | 92.6 | 94 | 96.2 | 93.4 | 93.68 |
| 11 | 94 | 94.1 | 95.1 | 97.4 | 94.6 | 95.04 |
| 12 | 95.2 | 95.2 | 96.6 | 98.4 | 95.6 | 96.12 |
| 13 | 96.2 | 96.2 | 96.8 | 99 | 96.2 | 96.88 |
| 14 | 96.7 | 97 | 97.6 | 99.6 | 96.7 | 97.52 |
| 15 | 97.6 | 97.8 | 98.4 | 100 | 97.2 | 98.2 |
| 16 | 98.4 | 98.4 | 99 | 100 | 97.8 | 98.72 |
| 17 | 99 | 99 | 99.4 | 100 | 98.1 | 99.1 |
| 18 | 99.6 | 99.5 | 99.7 | 100 | 98.4 | 99.44 |

-continued number of experiments 5

| Time | ASSAY 1 ml | ASSAY 2 ml | ASSAY 3 ml | ASSAY 4 ml | ASSAY 5 ml | AVERAGE ml |
|---|---|---|---|---|---|---|
| 19 | 100 | 99.8 | 99.8 | 100 | 98.4 | 99.6 |
| 20 | 100 | 100 | 99.8 | 100 | 98.4 | 99.64 |
| 21 | | | | | | |

Proportions for suppositories for children:
Na bicarbonate 0.350 g
K acid tartrate 0.575 g number of experiments 3

| Time | ASSAY 2 ml | ASSAY 3 ml | ASSAY 4 ml | AVERAGE ml |
|---|---|---|---|---|
| 1 | 16,2 | 15,4 | 14,4 | 15,33 |
| 2 | 25,8 | 25,4 | 24,6 | 25,27 |
| 3 | 32,8 | 32,8 | 32,1 | 32,57 |
| 4 | 37,9 | 38,2 | 37,8 | 37,97 |
| 5 | 42 | 42,2 | 41,8 | 42,00 |
| 6 | 45,1 | 45 | 44,8 | 44,97 |
| 7 | 47,2 | 47,4 | 47,2 | 47,27 |
| 8 | 48,8 | 49 | 48,9 | 48,90 |
| 9 | 49,9 | 50,4 | 50,1 | 50,13 |
| 10 | 50,6 | 51,6 | 51 | 51,07 |
| 11 | 51,4 | 52,7 | 51,9 | 52,00 |
| 12 | 52 | 53,3 | 52,6 | 52,63 |
| 13 | 52,4 | 53,6 | 53 | 53,00 |
| 14 | 52,6 | 54 | 53,4 | 53,33 |
| 15 | 53 | 54,4 | 53,8 | 53,73 |
| 16 | 53 | 54,6 | 54 | 53,87 |
| 17 | 52,3 | 54,9 | 54,2 | 53,80 |
| 18 | 54 | 55 | 54,2 | 54,40 |
| 19 | 54,2 | 55 | 54,2 | 54,47 |
| 20 | 54,4 | 55 | 54,2 | 54,53 |

I—Formulation Study According to the Invention Acid Saccharin

This ASSAY begins by the stoichiometric calculation to determine the required amount of saccharin to use without changing the amount of bicarbonate contained in the industrial formula.

Saccharin ($C_7H_5O_5NS$); 1 mole=183 g→$6.10^{-3}$ mole=1.119 g it is needed for suppositories for adult 1.119 g of acid saccharin.
it is requested for a suppository for children 1.119:2= 0.5595 g of acid saccharin

| Formula: | |
|---|---|
| Acid saccharin | 0.5595 g |
| Na bicarbonate | 0.350 g |

Bolt the saccharin before weighting it (bolter 0.315) Results for release:

number of experiments 2

| Time | ASSAY 0,5595 g ml | ASSAY 0,5595 g ml | AVERAGE ml |
|---|---|---|---|
| 1 | 24,00 | 27,00 | 25,80 |
| 2 | 28,40 | 33,40 | 30,90 |
| 3 | 32,10 | 37,50 | 34,80 |
| 4 | 35,00 | 40,30 | 37,65 |
| 5 | 37,40 | 42,60 | 40,00 |
| 6 | 39,40 | 44,40 | 41,90 |
| 7 | 41,30 | 45,80 | 43,55 |
| 8 | 42,90 | 47,00 | 44,95 |
| 9 | 44,20 | 48,00 | 46,10 |
| 10 | 45,40 | 48,80 | 47,10 |
| 11 | 46,50 | 49,40 | 47,95 |
| 12 | 47,40 | 50,20 | 48,80 |
| 13 | 48,10 | 50,80 | 49,45 |
| 14 | 48,80 | 51,30 | 50,05 |
| 15 | 49,40 | 51,50 | 50,45 |
| 16 | 50,00 | 51,80 | 50,90 |
| 17 | 50,40 | 51,90 | 51,15 |
| 18 | 50,80 | 52,00 | 51,40 |
| 19 | 51,20 | 52,40 | 51,70 |
| 20 | 51,60 | 52,40 | 52,00 |
| 21 | 51,80 | 52,60 | 52,20 |

II—Pyroglutamic Acid

Stoichiometric calculation:

Pyroglutamic acid ($C_5H_7O_5N$); 1 mole=147 g→$6.10^{-3}$ mole=0.899 g it is needed for a suppository for adult 0.899 g of pyroglutamic acid
it is needed for a suppository for children 0.899 g:2= 0.4495 g of pyroglutamic acid

| Formula: | |
|---|---|
| Pyroglutamic acid | 0.4495 g |
| Na bicarbonate | 0.350 g |

Reduction of the Amount of Pyroglutamic Acid

| Formula: | |
|---|---|
| Pyroglutamic acid | 0.400 g |
| Na bicarbonate | 0.350 g |

Conclusion

With pyroglutamic acid (0.4495 g) the same phenomenon as with acidic saccharin occurs: during the first two minutes the $CO_2$ release is important. With a little weaker pyroglutamic acid rate (0.400 g), the time for $CO_2$ release is a little shorter.

III—Crystalline Monopotassium Phosphate

Stoichiometric calculation:

Crystalline. Monopotassium phosphate($PO_4H_2K$);1 mole=136.09 g→$6.10^{-3}$ mole=0.832 g It is needed for a suppository for adults 0.832 g of monopotassium phosphate It is needed for a suppository for children 0.832 g :2== 0.416 g of monopotassium phosphate

| Formula: | |
|---|---|
| Monopotassium phosphate | 0.416 g |
| Na bicarbonate | 0.350 g |

Conclusion

Small $CO_2$ release.

Use a twofold amount with regard to the stoichiometric calculation.

Results for release:

| | number of experiments 3 | | | |
|---|---|---|---|---|
| Bicarb. 0,7 g Doses of monopotassium phosphate Time | ASSAY 0,832 g ml | ASSAY 0,832 g ml | ASSAY 0,832 g ml | AVERAGE ml |
| 1 | 15,2 | 13 | 12,8 | 13,67 |
| 2 | 22 | 19,8 | 20,4 | 20,73 |
| 3 | 27,6 | 25,4 | 26,5 | 26,50 |
| 4 | 32,6 | 30,1 | 31,8 | 31,50 |
| 5 | 36,9 | 34,2 | 36,2 | 35,77 |
| 6 | 40,6 | 37,7 | 40 | 39,43 |
| 7 | 43,9 | 40,9 | 43,4 | 42,73 |
| 8 | 46,8 | 43,5 | 46,1 | 45,47 |
| 9 | 49,1 | 45,8 | 48,6 | 47,83 |
| 10 | 51,4 | 48 | 50,8 | 50,07 |
| 11 | 53,3 | 49,8 | 52,7 | 51,93 |
| 12 | 54,8 | 51,3 | 54,2 | 53,43 |
| 13 | 56,2 | 52,7 | 55,7 | 54,87 |
| 14 | 57,4 | 54,1 | 56,9 | 56,13 |
| 15 | 58,5 | 55,4 | 58 | 57,30 |
| 16 | 59,6 | 56,5 | 58,8 | 58,30 |
| 17 | 60,4 | 57,4 | 59,7 | 59,17 |
| 18 | 61,1 | 58,4 | 60,5 | 60,00 |
| 19 | 61,8 | 59,2 | 61,1 | 60,70 |
| 20 | 62,4 | 59,8 | 61,6 | 61,27 |
| 21 | 63 | 60,3 | 62,1 | 61,80 |
| 22 | 63,4 | 60,9 | 62,6 | 62,30 |
| 23 | 63,8 | 61,4 | 63,1 | 62,77 |
| 24 | 64,3 | 62 | 63,4 | 63,23 |
| 25 | 64,7 | 62,4 | 63,8 | 63,63 |
| 26 | 65 | 62,6 | 64 | 63,87 |
| 27 | 65,2 | 62,8 | 64,3 | 64,10 |
| 28 | 65,4 | 63 | 64,5 | 64,30 |
| 29 | 65,5 | 63,2 | 64,5 | 64,40 |
| 30 | 65,6 | 63,2 | 64,5 | 64,43 |
| 31 | 65,8 | 63,2 | 64,5 | 64,50 |

IV—Anhydrous Monosodium Phosphate

Stoichiometric calculation:

Anhydrous monosodium phosphate $(NaH_2PO_4)$; 1 mole=119.98 g→$6.10^{-3}$ mole=0.734 g It is needed for a suppository for adults 0.734 g of monosodium phosphate It is needed for a suppository for children 0.734 g:2=0.366 g of monosodium phosphate Formula: twofold amount with regard to the stoichiometric calculation.

| Monosodium phosphate | 0.734 g |
|---|---|
| Na bicarbonate | 0.700 g |

Results of release

| | number of experiments 3 | | | |
|---|---|---|---|---|
| | Bicarb. 0.7 g | Screen 0.250 mm | | |
| Monopotassium Phosphate Time | ASSAY 0.734 g ml | ASSAY 0.734 g ml | ASSAY 0.734 g ml | AVERAGE ml |
| 1 | 16.2 | 16.5 | 13.6 | 15.43 |
| 2 | 24.2 | 24.9 | 21.2 | 23.43 |
| 3 | 30.4 | 31.8 | 28 | 30.07 |
| 4 | 35.5 | 37.3 | 33.8 | 35.53 |
| 5 | 39.8 | 41.9 | 38.6 | 40.10 |
| 6 | 43.3 | 45.5 | 42.2 | 43.67 |
| 7 | 46.2 | 48.8 | 45.4 | 46.80 |
| 8 | 48.7 | 51.3 | 48.1 | 49.37 |
| 9 | 50.9 | 53.6 | 50.4 | 51.63 |
| 10 | 52.7 | 55.5 | 52.4 | 53.53 |
| 11 | 54.2 | 57.2 | 54.1 | 55.17 |
| 12 | 55.6 | 58.6 | 55.6 | 56.60 |
| 13 | 56.9 | 59.7 | 57 | 57.87 |
| 14 | 58.2 | 60.9 | 58 | 59.03 |
| 15 | 59.2 | 51.8 | 59 | 60.00 |
| 16 | 60.2 | 62.4 | 59.6 | 60.73 |
| 17 | 61 | 63 | 60.3 | 61.43 |
| 18 | 61.6 | 63.4 | 60.8 | 61.93 |
| 19 | 62.2 | 63.8 | 61.2 | 62.40 |
| 20 | 62.6 | 64.1 | 61.6 | 62.77 |
| 21 | 63.1 | 64.4 | 61.9 | 63.13 |
| 22 | 63.4 | 64.6 | 62.1 | 63.37 |
| 23 | 63.8 | 64.8 | 62.3 | 63.63 |
| 24 | 64.2 | 64.9 | 62.5 | 63.87 |
| 25 | 64.5 | 64.9 | 62.6 | 64.00 |
| 26 | 64.6 | 64.9 | 62.8 | 64.10 |
| 27 | 64.8 | 64.9 | 62.8 | 64.17 |
| 28 | 64.9 | 64.9 | 62.8 | 64.20 |
| 29 | 65 | 64.9 | 62.8 | 64.23 |

V—Succinimide

Stoichiometric calculation

Succinimide $(C_4H_5NO_2)$; 1 mole=99.09 g→$6.10^{-3}$ mole=0.606 g

It is needed for a suppository for adults 0.606 g of Succinimide

It is needed for a suppository for children 0.606 g:2=0.303 g of Succinimide

| Formula | |
|---|---|
| Succinimide | 0.303 g |
| Na bicarbonate | 0.305 g |

Results for release: (see table)

Conclusion $CO_2$ release is very small with respect to the specified amounts of active principles by the stoichiometric calculation.

| NUMBER OF ASSAYS |  |
|---|---|
| 1 | |
| Time | ASSAY 0.303 g ml |
| 1 | 2.0 |
| 2 | 2.6 |
| 3 | 3.1 |
| 4 | 3.4 |
| 5 | 3.7 |
| 6 | 4.1 |
| 7 | 4.4 |
| 8 | 4.7 |
| 9 | 5.1 |
| 10 | 5.3 |
| 11 | 5.6 |
| 12 | 5.9 |
| 13 | 6.1 |
| 14 | 6.3 |
| 15 | 6.6 |
| 16 | 6.8 |
| 17 | 7.0 |
| 18 | 7.3 |
| 19 | 7.5 |
| 20 | 7.6 |
| 21 | 7.8 |
| 22 | 7.9 |
| 23 | 8.0 |
| 24 | 8.1 |
| 25 | 8.2 |
| 26 | 8.3 |

B-Galenic Assay for Suppositories with Anhydrous Monosodium Phosphate

To have a satisfactory $CO_2$ release, two-fold of the stoichiometric amount has been to be introduced.

Reference Formula for Children

| K acid tartrate | 0.575 g |
|---|---|
| Na bicarbonate | 0.350 g |
| Soya lecithin | 0.105 g |
| Talc | 0.0525 g |
| SUPPOCIRE ® | 0.9175 g |
| | 2.000 g |

Use of anhydrous monosodium phosphate instead of K acid tartrate:

| Formula: | |
|---|---|
| Anhydrous monosodium phosphate | 0.734 g |
| Na bicarbonate | 0.700 g |
| Soya lecithin | 0.105 g |
| Talc | 0.0525 g |
| SUPPOCIRE ® | 0.4085 g |
| | 2.000 g |

Calculated for 10 suppositories.

Results

The manufacture of the suppositories has been proved difficult because it has been requested to heat until 60° C. to fill up the alveolus on the one hand and the bulk was too pasty and granular on the other hand. This difficulty can be due to the small amount of SUPPOCIRE® used. The $CO_2$ release assay made after 24 hours is indicated in the table hereafter.

| Time | ASSAY 2.3738 g ml | ASSAY 2,3687 g ml | ASSAY 2.4 g ml | AVERAGE 2.38083 g ml | CORRECT 2 g ml |
|---|---|---|---|---|---|
| 1 | 4.5 | 6 | 6.2 | 5.57 | 4.68 |
| 2 | 23.4 | 23.2 | 26.6 | 24.40 | 20.50 |
| 3 | 34.8 | 34.4 | 40.2 | 36.47 | 30.63 |
| 4 | 43.4 | 42.2 | 49.4 | 45.00 | 37.80 |
| 5 | 49.8 | 48.5 | 56.1 | 51.47 | 43.23 |
| 6 | 54.6 | 52.3 | 61.1 | 56.00 | 47.04 |
| 7 | 58.3 | 55.2 | 64.8 | 59.43 | 49.93 |
| 8 | 61.1 | 58.2 | 67.8 | 62.37 | 52.39 |
| 9 | 63.2 | 60.7 | 69.8 | 64.57 | 54.24 |
| 10 | 65 | 63 | 71.4 | 66.47 | 55.84 |
| 11 | 66.3 | 64.8 | 72.6 | 67.90 | 57.04 |
| 12 | 67.5 | 66.1 | 73.6 | 69.07 | 58.02 |
| 13 | 68.4 | 67.2 | 74.1 | 69.90 | 58.72 |
| 14 | 69.1 | 68.4 | 74.8 | 70.77 | 59.45 |
| 15 | 69.8 | 69.4 | 75.4 | 71.53 | 60.09 |
| 16 | 70.4 | 70.3 | 75.8 | 72.17 | 60.62 |
| 17 | 71 | 71.4 | 76.2 | 72.87 | 61.21 |
| 18 | 71.6 | 72.2 | 76.4 | 73.40 | 61.66 |
| 19 | 72 | 72.8 | 76.8 | 73.87 | 62.05 |
| 20 | 72.4 | 73.3 | 77 | 74.23 | 62.36 |
| 21 | 72.7 | 73.6 | 77.2 | 74.50 | 62.58 |
| 22 | 72.8 | 74 | 77.2 | 74.67 | 62.72 |
| 23 | 72.9 | 74.3 | 77.2 | 74.80 | 62.84 |
| 24 | 73.2 | 74.7 | 77.2 | 75.03 | 63.03 |
| 25 | 73.2 | 75 | 77.2 | 75.13 | 63.12 |
| 26 | 73.2 | 75.4 | 77.2 | 75.27 | 63.23 |
| 27 | 73.2 | 75.4 | 77.2 | 75.30 | 63.26 |
| 28 | 73.2 | 75.7 | 77.2 | 75.37 | 63.31 |

Conclusion

The comparison of the obtained curves with tartrate plus Na bicarbonate on one hand the $NaPO_4H$ plus Na bicarbonate on the other hand with the curves of the $NaPO_4H$ and Na bicarbonate suppositories shows that there is no reaction between the powder and the excipient. The suppositories provide a curve identical to the one of the mixture of powders alone.

| | number of experiments | 3 | |
|---|---|---|---|
| Time | ASSAY TARTRATE ml | ASSAY HPO4Na ml | AVERAGE Suppository 2 g ml |
| 1 | 15.33 | 15.43 | 4.68 |
| 2 | 25.27 | 23.43 | 20.5 |
| 3 | 32.57 | 30.07 | 30.63 |
| 4 | 37.97 | 35.53 | 37.8 |
| 5 | 42.00 | 40.1 | 43.23 |
| 6 | 44.97 | 43.67 | 47.04 |
| 7 | 47.27 | 46.8 | 49.93 |
| 8 | 48.90 | 49.37 | 52.39 |
| 9 | 50.13 | 51.63 | 54.24 |
| 10 | 51.07 | 53.53 | 55.84 |
| 11 | 52.00 | 55.17 | 57.04 |
| 12 | 52.63 | 56.6 | 58.02 |
| 13 | 53.00 | 57.87 | 58.72 |
| 14 | 53.33 | 59.03 | 59.45 |
| 15 | 53.73 | 60 | 60.09 |
| 16 | 53.87 | 60.73 | 60.62 |
| 17 | 53.80 | 61.43 | 61.21 |
| 18 | 54.40 | 61.93 | 61.66 |
| 19 | 54.47 | 62.4 | 62.05 |
| 20 | 54.53 | 62.77 | 62.36 |
| 21 | 54.53 | 63.13 | 62.58 |
| 22 | | 63.37 | 62.72 |
| 23 | | 63.63 | 62.84 |

-continued

| Time | ASSAY TARTRATE ml | ASSAY HPO4Na ml | AVERAGE Suppository 2 g ml |
|---|---|---|---|
| | number of experiments | 3 | |
| 24 | | 63.87 | 63.03 |
| 25 | | 64 | 63.12 |
| 26 | | 64.1 | 63.23 |
| 27 | | 64.17 | 63.26 |
| 28 | | 64.2 | 63.31 |
| 29 | | 64.23 | |

Comparison of the Different NaPO4H2 Titrations

The following table shows the regrouped results about the different titrations of the anhydrous monosodium phosphate suppositories with regard to the 2 g suppositories obtained by industrial manufacture and to the 2 g suppositories manufactured in the Galen cal laboratory.

| Time | Industrial average 2 g | Laboratory average 2 g | PO4HNa 0.592 g Laboratory average 2 g | PO4HNa 0.5624 Laboratory average 2 g | PO4HNa 0.497 g Laboratory average 2 g | PO4HNa 0.367 g Laboratory average 2 g |
|---|---|---|---|---|---|---|
| 0 | 0.00 | 0.00 | 0.00 | 0.00 | 0.00 | 0.00 |
| 1 | 2.20 | 3.48 | 5.88 | 4.79 | 3.83 | 3.63 |
| 2 | 5.20 | 9.00 | 16.79 | 13.19 | 9.69 | 7.04 |
| 3 | 8.61 | 14.95 | 22.67 | 19.24 | 14.51 | 10.02 |
| 4 | 11.97 | 20.10 | 27.52 | 24.03 | 18.80 | 12.62 |
| 5 | 15.21 | 24.37 | 31.50 | 28.20 | 22.34 | 14.68 |
| 6 | 18.24 | 27.52 | 35.14 | 31.46 | 25.33 | 16.47 |
| 7 | 20.95 | 30.39 | 38.25 | 34.25 | 27.24 | 17.99 |
| 8 | 23.51 | 32.68 | 41.02 | 36.79 | 29.84 | 19.23 |
| 9 | 25.98 | 34.59 | 43.27 | 38.79 | 31.78 | 20.26 |
| 10 | 28.18 | 36.35 | 45.52 | 40.48 | 33.36 | 21.13 |
| 11 | 30.42 | 37.78 | 47.34 | 41.99 | 34.79 | 21.89 |
| 12 | 32.55 | 39.11 | 48.98 | 43.34 | 36.01 | 22.65 |
| 13 | 34.52 | 40.34 | 50.54 | 44.49 | 37.09 | 23.19 |
| 14 | 36.29 | 41.49 | 51.84 | 45.40 | 38.08 | 23.73 |
| 15 | 38.02 | 42.58 | 53.14 | 46.19 | 38.90 | 24.06 |
| 16 | 39.56 | 43.69 | 54.09 | 46.88 | 39.59 | 24.60 |
| 17 | 41.06 | 44.61 | 55.04 | 47.47 | 40.20 | 25.14 |
| 18 | 42.39 | 45.59 | 55.91 | 47.97 | 40.89 | 25.68 |
| 19 | 43.73 | 46.32 | 56.60 | 48.44 | 41.32 | 26.12 |
| 20 | 44.86 | 47.11 | 57.29 | 48.85 | 41.78 | 26.55 |
| 21 | 45.89 | 47.72 | 57.81 | 49.19 | 42.03 | 26.87 |
| 22 | 46.79 | 48.39 | 58.16 | 49.45 | 42.29 | 27.15 |
| 23 | 47.56 | 49.01 | 58.42 | 49.66 | 42.54 | 27.42 |
| 24 | 48.26 | 49.48 | 58.76 | 49.88 | 42.72 | 27.63 |
| 25 | 48.83 | 50.04 | 59.20 | 50.04 | 42.95 | 27.85 |
| 26 | 49.40 | 50.53 | 59.54 | 50.13 | 43.05 | 28.07 |
| 27 | 49.80 | 50.97 | 59.71 | 50.29 | 43.13 | 28.28 |
| 28 | 50.23 | 51.40 | 59.89 | 50.39 | 43.23 | 28.39 |
| 29 | 50.56 | 51.74 | 60.41 | 50.45 | 43.23 | 28.50 |
| 30 | 50.83 | 52.10 | 60.75 | 50.45 | | 28.61 |

Preservation Study of the Suppository Preparations with Adult Proportions by Ageing at Ambient Temperature (20° C.) in a Thermostated Bath Controlled Hygrometry Reference Formula Reference formula manufactured in the Galen cal laboratory:

| | |
|---|---|
| K acid tartrate | 1.150 g |
| Na bicarbonate | 0.700 g |
| Soya lecithin | 0.210 g |
| Talc | 0.105 g |
| SUPPOCIRE ® | 1.835 g |
| | 4.000 g |

Results

Good homogeneity of the batch.

| Time | ASSAY 1 3.9058 ml | ASSAY 2 3.9226 ml | ASSAY 3 3.9246 ml | AVERAGE 3.9177 ml |
|---|---|---|---|---|
| 5 | 44.5 | 31.5 | 42 | 39.33 |
| 10 | 73 | 63 | 72 | 69.33 |
| 20 | 100.5 | 96 | 100.5 | 99.00 |
| 40 | 108.5 | 110 | 112.5 | 110.33 |

Corrected to 4 g

| Time | ASSAY 1 4.0000 ml | ASSAY 2 4.0000 ml | ASSAY 3 4.0000 ml | AVERAGE 4.0000 ml |
|---|---|---|---|---|
| 5 | 45.6 | 32.1 | 42.8 | 40.2 |
| 10 | 74.8 | 64.2 | 73.4 | 70.8 |
| 20 | 102.9 | 97.9 | 102.4 | 101.1 |
| 40 | 111.1 | 112.2 | 114.7 | 112.6 |

Compositions According to the Invention

1—With monosodium phosphate

| Formula | |
|---|---|
| Monosodium phosphate | 1.184 g |
| Na bicarbonate | 1.128 g |
| Soya lecithin | 0.210 g |
| Talc | 0.105 g |
| SUPPOCIRE ® | 1.373 g |
| | 4.000 g |

Results

Good bulk homogeneity

| Time | ASSAY 1 4.6744 ml | ASSAY 2 4.4121 ml | ASSAY 3 4.3818 ml | AVERAGE 4.4894 ml |
|---|---|---|---|---|
| 5 | 71.5 | 59 | 64 | 64.83 |
| 10 | 94 | 84 | 85 | 84.67 |
| 20 | 121 | 107.5 | 110 | 112.83 |
| 40 | 134 | 121.5 | 126 | 127.17 |

Corrected to 4 g

| Time | ASSAY 1 4.0000 ml | ASSAY 2 4.0000 ml | ASSAY 3 4.0000 ml | AVERAGE 4.0000 ml |
|---|---|---|---|---|
| 5 | 61.2 | 53.5 | 58.4 | 57.7 |
| 10 | 80.4 | 76.2 | 77.6 | 78.1 |
| 20 | 103.5 | 97.5 | 100.4 | 100.5 |
| 40 | 114.7 | 110.2 | 115.0 | 113.3 |

2—With Glutamic acid

| Forumla: | |
|---|---|
| Glutamic acid | 0.878 g |
| Sodium bicarbonate | 0.700 g |
| Soya lecithin | 0.210 g |
| Talc | 0.105 g |
| SUPPOCIRE ® | 2.107 g |
| | 4.000 g |

Results

Homogeneous batch.

| Time | ASSAY 1 3,5728 ml | ASSAY 2 3,6235 ml | AVERAGE 3,5982 ml |
|---|---|---|---|
| 5 | 58 | 57,5 | 57,75 |
| 10 | 85 | 81,5 | 83,25 |
| 20 | 97,5 | 100 | 98,75 |
| 40 | 101 | 102 | 101,50 |

Corrected to 4 g

| Time | ASSAY 1 4,0000 ml | ASSAY 2 4,0000 ml | AVERAGE 4,0000 ml |
|---|---|---|---|
| 5 | 64,9 | 63,5 | 64,2 |
| 10 | 95,2 | 90,0 | 92,6 |
| 20 | 109,2 | 110,4 | 109,8 |
| 40 | 113,1 | 112,6 | 112,8 |

3—With pyroglutamic acid

| | |
|---|---|
| Pyroglutamic acid | 0.889 g |
| Sodium bicarbonate | 0.700 g |
| Soya lecithin | 0.210 g |
| Talc | 0.105 g |
| SUPPOCIRE ® | 2.096 g |
| | 4.000 g |

Results: Homogeneous Bulk

| Time | ASSAY 1 3,7341 ml | ASSAY 2 3,7351 ml | ASSAY 3 3,5711 ml | AVERAGE 3,6801 |
|---|---|---|---|---|
| 5 | 47 | 55 | 43 | 48,33 |
| 10 | 89,5 | 92,5 | 81,5 | 87,83 |
| 20 | 107,5 | 103 | 97 | 102,50 |
| 40 | 110 | 103 | 100 | 104,33 |

Corrected to 4 g

| Time | ASSAY 1 4,0000 ml | ASSAY 2 4,0000 ml | ASSAY 3 4,0000 ml | AVERAGE 4,0000 ml |
|---|---|---|---|---|
| 5 | 50,3 | 58,9 | 48,2 | 52,5 |
| 10 | 95,9 | 99,1 | 91,3 | 95,4 |
| 20 | 115,2 | 110,3 | 108,6 | 111,4 |
| 40 | 117,8 | 110,3 | 112,0 | 113,4 |

4—with monosodium citrate

| Formula: | |
|---|---|
| Monosodium citrate | 1.2847 g |
| Sodium bicarbonate | 0.700 g |
| Soya lecithin | 0.210 g |
| Talc | 0.105 g |
| SUPPOCIRE ® | 1.7003 g |
| | 4.000 g |

Results: Homogeneous Bulk.

| Time | ASSAY 1 3,9785 ml | ASSAY 2 4,148 ml | AVERAGE 4,0633 ml |
|---|---|---|---|
| 5 | 98 | 110 | 104,00 |
| 10 | 124 | 131 | 127,50 |
| 20 | 142,5 | 147 | 144,75 |
| 40 | 149,5 | 149 | 149,25 |

Corrected to 4 g

| Time | ASSAY 1 4,0000 ml | ASSAY 2 4,0000 ml | AVERAGE 4,0000 ml |
|---|---|---|---|
| 5 | 98,5 | 106,1 | 102,3 |
| 10 | 124,7 | 126,3 | 125,5 |
| 20 | 143,3 | 141,8 | 142,5 |
| 40 | 150,3 | 143,7 | 147,0 |

Comparative Study of Preservation for Various Bulks After Three Months

Assembly of the curves were collected on the same figure for a general view of the results.

Results

Curve 1: After ageing of 3 months the $CO_2$ release has clearly increased.

Curve 2: $CO_2$ release similar during the first 10 minutes and a little variation at the end.

Curve 3: increase of the $CO_2$ release

Curve 4: $CO_2$ decrease. It is the only of the 5 products which has released the lesser of $CO_2$ after 3 months Curve 5: Increase of the $CO_2$ release

| | The first day | | | | |
|---|---|---|---|---|---|
| Time | CURVE 1 Reference suppositories ml | CURVE 2 Mono Na phosphate ml | CURVE 3 Glutamic acid ml | CURVE 4 Pyroglutamic acid ml | CURVE 5. Mono citrate Na ml |
| 5 | 26,65 | 59,4 | 41,2 | 88,9 | 70,52 |
| 10 | 52,31 | 76 | 66,6 | 107,16 | 96,99 |
| 20 | 77,31 | 93,3 | 88,5 | 122,58 | 120,97 |
| 40 | 92,93 | 99,6 | 96,7 | | 132,51 |

| | After 3 months | | | | |
|---|---|---|---|---|---|
| Time | CURVE 1 Reference suppositories ml | CURVE 2 Mono Na phosphate ml | CURVE 3 Glutamic acid ml | CURVE 4 Pyroglutamic acid ml | CURVE 5 Mono Na citrate ml |
| 5 | 40.2 | 57.7 | 64.2 | 52.5 | 102.3 |
| 10 | 92.2 | 78.1 | 92.6 | 95.4 | 125.5 |
| 20 | 117.0 | 100.5 | 109.8 | 111.4 | 142.5 |
| 40 | 121.6 | 113.3 | 112.8 | 113.4 | 147.0 |

The FIG. 1/1 collects the obtained results. The symbol A defines the values on the first day of manufacturing. The symbol B defines the values after preservation of 3 months.

Conclusion

After a 3 months preservation period, the control results of $CO_2$ release show a very clear increase for the formulations 1, 3 and 5.

This phenomenon may be explained by a come back to stable state of the semi-synthetic glycerides showing a decrease of the crushing strength with as a consequence a better reactivity between the components in some formulas.

On the other hand, formulations 2 and 4 release after preservation, an amount of $CO_2$ about the same than after manufacture.

What is claimed is:

1. A pharmaceutical composition for rectal administration formed with an effervescent mixture of sodium bicarbonate and glutamic acid with at least one diluent adapted for rectal administration.

2. A composition of claim 1 in the form of a suppository.

3. A composition of claim 1 in the form of rectal capsules.

4. A pharmaceutical composition for rectal administration formed with an effervescent mixture of sodium bicarbonate and pyroglutamic acid with at least one diluent adapted for rectal administration.

5. A composition of claim 4 containing about 0.700 g of sodium bicarbonate and 0.85 to 0.90 g of pyroglutamic acid.

6. A composition of claim 4 in the form of a suppository.

7. A composition of claim 4 in the form of rectal capsules.

8. A pharmaceutical composition for rectal administration formed with about 0.700 g of sodium bicarbonate and 1.15 to 1.20 g of monosodium phosphate with at least one diluent adapted for rectal administration.

* * * * *